United States Patent
Wu et al.

(10) Patent No.: US 11,648,541 B2
(45) Date of Patent: May 16, 2023

(54) METHODS OF PREPARING AN AROMATIZATION CATALYST

(71) Applicant: Chevron Phillips Chemical Company LP, The Woodlands, TX (US)

(72) Inventors: An-Hsiang Wu, Kingwood, TX (US); Joseph Bergmeister, Spring, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 8 days.

(21) Appl. No.: 17/552,959

(22) Filed: Dec. 16, 2021

(65) Prior Publication Data

US 2022/0134319 A1 May 5, 2022

Related U.S. Application Data

(60) Division of application No. 16/660,469, filed on Oct. 22, 2019, now Pat. No. 11,260,376, which is a continuation-in-part of application No. 15/386,129, filed on Dec. 21, 2016, now Pat. No. 10,487,025.

(51) Int. Cl.

| | |
|---|---|
| *B01J 29/62* | (2006.01) |
| *B01J 21/08* | (2006.01) |
| *B01J 35/00* | (2006.01) |
| *B01J 35/02* | (2006.01) |
| *B01J 37/08* | (2006.01) |
| *B01J 37/26* | (2006.01) |
| *B01J 37/24* | (2006.01) |
| *B01J 37/02* | (2006.01) |
| *C07C 5/41* | (2006.01) |
| *B01J 37/06* | (2006.01) |
| *B01J 23/42* | (2006.01) |
| *B01J 27/12* | (2006.01) |
| *B01J 27/10* | (2006.01) |
| *B01J 37/00* | (2006.01) |
| *B01J 27/128* | (2006.01) |
| *B01J 29/068* | (2006.01) |
| *B01J 29/072* | (2006.01) |
| *B01J 37/22* | (2006.01) |
| *B01J 29/63* | (2006.01) |

(52) U.S. Cl.
CPC .............. *B01J 29/62* (2013.01); *B01J 21/08* (2013.01); *B01J 23/42* (2013.01); *B01J 27/10* (2013.01); *B01J 27/12* (2013.01); *B01J 27/128* (2013.01); *B01J 29/068* (2013.01); *B01J 29/072* (2013.01); *B01J 29/63* (2013.01); *B01J 35/002* (2013.01); *B01J 35/0006* (2013.01); *B01J 35/026* (2013.01); *B01J 37/0009* (2013.01); *B01J 37/0201* (2013.01); *B01J 37/0207* (2013.01); *B01J 37/0209* (2013.01); *B01J 37/0236* (2013.01); *B01J 37/06* (2013.01); *B01J 37/08* (2013.01); *B01J 37/22* (2013.01); *B01J 37/24* (2013.01); *B01J 37/26* (2013.01); *C07C 5/417* (2013.01); *B01J 2229/18* (2013.01); *B01J 2229/186* (2013.01); *B01J 2229/20* (2013.01); *B01J 2229/42* (2013.01); *C07C 2521/08* (2013.01); *C07C 2523/42* (2013.01); *C07C 2527/08* (2013.01); *C07C 2527/10* (2013.01); *C07C 2527/12* (2013.01); *C07C 2527/13* (2013.01); *C07C 2529/068* (2013.01); *C07C 2529/072* (2013.01); *C07C 2529/62* (2013.01)

(58) Field of Classification Search
CPC ................. Y02P 20/52; C07C 2521/08; C07C 2523/42; C07C 2527/08; C07C 2527/10; C07C 2527/12; C07C 2527/13; C07C 2529/068; C07C 2529/072; C07C 2529/62; B01J 21/08; B01J 23/42; B01J 27/10; B01J 27/12; B01J 27/128; B01J 29/62; B01J 29/63; B01J 29/068; B01J 29/072; B01J 2229/18; B01J 2229/186; B01J 2229/42; B01J 2229/20; B01J 35/002; B01J 35/0006; B01J 35/026; B01J 37/0009; B01J 37/0201; B01J 37/0207; B01J 37/0209; B01J 37/0236; B01J 37/06; B01J 37/08; B01J 37/22; B01J 37/24; B01J 37/26
USPC ....................... 502/60, 63, 64, 66, 68, 69, 74
See application file for complete search history.

(56) References Cited

U.S. PATENT DOCUMENTS

| | | |
|---|---|---|
| 3,216,789 A | 11/1965 | Breck |
| 3,594,331 A | 7/1971 | Elliott, Jr. |
| 4,670,614 A | 6/1987 | Ushio |
| 4,681,865 A | 7/1987 | Katsuno |
| 4,987,109 A | 1/1991 | Kao |
| 5,354,933 A | 10/1994 | Ohashi |
| 5,558,851 A | 9/1996 | Miller |
| 6,190,539 B1 | 2/2001 | Holtermann |
| 6,207,042 B1 | 3/2001 | Holtermann |
| 6,518,470 B1 | 2/2003 | Fukunaga |

(Continued)

FOREIGN PATENT DOCUMENTS

| | | |
|---|---|---|
| EP | 0201856 B1 | 1/1991 |
| EP | 2170509 B1 | 8/2015 |

OTHER PUBLICATIONS

International Search Report and Written Opinion, PCT/US2017/066257, dated Apr. 17, 2018, 27 pages.

(Continued)

*Primary Examiner* — Elizabeth D Wood
(74) *Attorney, Agent, or Firm* — Brandon N. Hudder

(57) ABSTRACT

Catalysts and method of preparing the catalysts are disclosed. One of the catalysts includes a zeolite support, a Group VIII metal on the zeolite support, and at least two halides bound to the zeolite support, to the Group VIII metal, or to both, and can have an average crush strength greater than 11.25 lb based on at least two samples of pellets of the catalyst measured in accordance with ASTM D4179.

16 Claims, No Drawings

(56) References Cited

U.S. PATENT DOCUMENTS

| | | |
|---|---|---|
| 6,812,180 B2 | 11/2004 | Fukunaga |
| 7,153,801 B2 | 12/2006 | Wu |
| 7,902,105 B2 | 3/2011 | Khare |
| 8,263,518 B2 | 9/2012 | Khare |
| 8,664,145 B2 | 3/2014 | Wu |
| 8,835,341 B2 | 9/2014 | Khare |
| 2004/0259719 A1 | 12/2004 | Wu |
| 2009/0156871 A1 | 6/2009 | Khare |
| 2010/0081565 A1 | 4/2010 | Quick |
| 2013/0035530 A1 | 2/2013 | Khare |
| 2014/0088333 A1 | 3/2014 | Khare |
| 2017/0128920 A1 | 5/2017 | Wu |
| 2018/0065115 A1 | 3/2018 | Alvez-Manoli |
| 2018/0169638 A1 | 6/2018 | Snell |

OTHER PUBLICATIONS

International Search Report and Written Opinion, PCT/US2020/051267, dated Dec. 7, 2020, 11 pages.

US 11,648,541 B2

METHODS OF PREPARING AN AROMATIZATION CATALYST

CROSS-REFERENCE TO RELATED APPLICATIONS

The present application is a divisional of and claims priority to U.S. patent application Ser. No. 16/660,469 filed Oct. 22, 2019, now U.S. Pat. No. 11,260,376, which is a continuation-in-part of and claims priority to U.S. patent application Ser. No. 15/386,129 filed Dec. 21, 2016, now U.S. Pat. No. 10,487,025 B2, entitled "Methods of Preparing an Aromatization Catalyst," both of which are incorporated by reference herein in their entirety.

FIELD

The present disclosure relates to aromatization of hydrocarbons with an aromatization catalyst. Specifically, this disclosure relates to methods of preparing an aromatization catalyst.

BACKGROUND

The catalytic conversion of hydrocarbons into aromatic compounds, referred to as aromatization, is an important industrial process used to produce fundamental building block chemicals on which a large portion of the chemical industry is based. Aromatization reactions may include the dehydrogenation, isomerization, and hydrocracking of hydrocarbons. These reactions are generally conducted in one or more aromatization reactors containing aromatization catalysts. These catalysts may increase the selectivity to desired aromatics, and/or the conversion rates of the reactions to the desired aromatic compounds. Given their commercial importance, an ongoing need exists for improved methods of preparing aromatization catalysts with high selectivity and conversion.

Additionally, movement of catalyst particles during catalyst loading and while the reactor is on stream creates catalyst fines. For example, transfer of catalyst from catalyst storage drums to an aromatization reactor causes catalyst particles to contact one another and to make contact with the transfer equipment. The contact may cause the catalyst particles to break. The fines are created when small pieces of the catalyst break away from either the broken or unbroken catalyst particles. Fines can also be generated during process upsets which can induce movement in the catalyst bed leading to broken and abraded catalyst particles. The catalyst fines are abrasive to the inner surface of the reactor, and they can plug equipment associated with the reactor, such as strainers and pumps.

SUMMARY

Disclosed herein is a catalyst comprising a zeolite support; a Group VIII metal on the zeolite support; and at least two halides bound to the zeolite support, to the Group VIII metal, or to both, wherein an average crush strength of the catalyst is greater than 11.25 lb based on at least two samples of pellets of the catalyst measured in accordance with ASTM D4179.

Also disclosed herein is a method of preparing a catalyst comprising calcining an extruded base to form a calcined extruded base, wherein the extruded base comprises a KL-zeolite, contacting the calcined extruded base with a first fluorine-containing compound to form a fluorinated calcined extruded base, washing the fluorinated calcined extruded base to form a washed fluorinated calcined extruded base, drying the washed fluorinated calcined extruded base to form a dried washed fluorinated calcined extruded base, calcining the dried washed fluorinated calcined extruded base to form a bound zeolite support, and contacting the bound zeolite support with a Group VIII metal and a second fluorine-containing compound, wherein the first fluorine-containing compound and the second fluorine-containing compound may be the same or different.

DETAILED DESCRIPTION

It should be understood at the outset that although an illustrative implementation of one or more aspects are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Disclosed herein are methods of preparing catalysts. In an aspect, the catalyst is an aromatization catalyst that is used to convert hydrocarbons into aromatic compounds. Generally, these conversions of hydrocarbons into aromatics are carried out in one or more aromatization reactors. Hereinafter, the disclosure will focus on preparation of an aromatization catalyst which may be referred to generally as the "catalyst." However, it is contemplated that one of ordinary skill in the art with the benefits of this disclosure may employ similar methodologies to prepare other catalyst types. In an aspect, the catalysts disclosed herein comprise a bound zeolite support, one or more catalytically active metals, and one or more halides.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), may be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

In this disclosure, while compositions and methods are often described in terms of "comprising" various components or steps, the compositions and methods may also "consist essentially of" or "consist of" the various components or steps, unless stated otherwise.

The terms "a," "an," and "the" are intended to include plural alternatives, e.g., at least one. For instance, the disclosure of "a transition metal" or "a halogen," is meant to encompass one, or mixtures or combinations of more than one, transition metal or halogen, unless otherwise specified.

For any particular compound or group disclosed herein, any name or structure (general or specific) presented is intended to encompass all conformational isomers, regioisomers, stereoisomers, and mixtures thereof that may arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes n-hexane, 2-methyl-pentane, 3-methyl-pentane, 2,2-dimethyl-butane, and 2,3-dimethyl-butane; and a general reference to a butyl group includes an n-butyl group, a sec-butyl group, an iso-butyl group, and a t-butyl group.

In one aspect, a chemical "group" may be defined or described according to how that group is formally derived from a reference or "parent" compound, for example, by the number of hydrogen atoms removed from the parent compound to generate the group, even if that group is not literally synthesized in such a manner. These groups may be utilized as substituents, or coordinated, or bonded to metal atoms. By way of example, an "alkyl group" formally may be derived by removing one hydrogen atom from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Various numerical ranges are disclosed herein. When a range of any type is disclosed or claimed herein, the intent is to disclose or claim individually each possible number that such a range could reasonably encompass, including end points of the range as well as any sub-ranges and combinations of sub-ranges encompassed therein, unless otherwise specified. As a representative example, the present application discloses that the bound zeolite support comprises fluoride present in an amount of from about 0.1 wt. % to about 5 wt. %. By a disclosure that the bound zeolite support contains an amount of fluoride that may be present in the range of about 0.1 wt. % to about 5 wt. %, the intent is to recite that the amount of fluoride may be any amount within the range and, for example, may be equal to about 0.5 wt. %, about 1.0 wt. %, about 1.5 wt. %, about 2.0 wt. %, about 2.5 wt. %, about 3.0 wt. %, about 3.5 wt. %, about 4.0 wt. %, about 4.5 wt. %, or about 5.0 wt. %. Additionally, the amount of fluoride may be within any range from about 0.1 wt. % to about 5 wt. % (for example, the amount of fluoride may be in a range from about 0.2 wt. % to about 1.5 wt. %), and this also includes any combination of ranges such as between about 0.3 wt. % to about 1.8 wt. %. Likewise, all other ranges disclosed herein should be interpreted in a manner similar to this example.

As used herein, the term "hydrocarbon" refers to a compound containing only carbon and hydrogen atoms. Other identifiers may be utilized to indicate the presence of particular groups, if any, in the hydrocarbon (e.g., halogenated hydrocarbon indicates the presence of one or more halogen atoms replacing an equivalent number of hydrogen atoms in the hydrocarbon).

An "aromatic" compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds, e.g., benzene, toluene, and xylenes) and "heteroarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" may be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers may be utilized to indicate the presence of particular groups, if any, in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group may be linear or branched unless otherwise specified.

A "cycloalkane" is a saturated cyclic hydrocarbon, with or without side chains, for example, cyclobutane, cyclopentane, cyclohexane, methyl cyclopentane, and methyl cyclohexane. Other identifiers may be utilized to indicate the presence of particular groups, if any, in the cycloalkane (e.g., halogenated cycloalkane indicates the presence of one or more halogen atoms replacing an equivalent number of hydrogen atoms in the cycloalkane).

The term "halogen" has its usual meaning. Examples of halogens include fluorine, chlorine, bromine, and iodine.

Molar selectivities are defined as:

$$\text{Benzene selectivity: } S_{Bz} = \frac{\dot{n}_{Bz,prod}}{\dot{n}_{convC6,feed} - \dot{n}_{convC6,prod}} \quad \text{Eq. 1}$$

$$\text{Toluene selectivity: } S_{Tol} = \frac{\dot{n}_{Tol,prod}}{\dot{n}_{convC7,feed} - \dot{n}_{convC7,prod}} \quad \text{Eq. 2}$$

$$\text{Benzene + Toluene selectivity: } S_{Bz+Tol} = \quad \text{Eq. 3}$$
$$\frac{\dot{n}_{Bz,prod} + \dot{n}_{Tol,prod}}{\dot{n}_{convC6,C7,feed} - \dot{n}_{convC6,C7,prod}}$$

$$\text{Aromatics selectivity: } S_{arom} = \frac{\dot{n}_{Bz,prod} + \dot{n}_{Tol,prod} + \dot{n}_{C8+arom,prod}}{\dot{n}_{convC6-C8+,feed} - \dot{n}_{convC6-C8+,prod}} \quad \text{Eq. 4}$$

Conversion is defined as the number of moles converted per mol of "convertible" components fed: wherein ṅ indicates a molar flow rate in a continuous reactor or the number of moles in a batch reactor.

$$C6 \text{ conversion: } X_{C6} = \frac{\dot{n}_{convC6,feed} - \dot{n}_{convC6,prod}}{\dot{n}_{convC6,feed}} \quad \text{Eq. 5}$$

$$C7 \text{ conversion: } X_{C7} = \frac{\dot{n}_{convC7,feed} - \dot{n}_{convC7,prod}}{\dot{n}_{convC7,feed}} \quad \text{Eq. 6}$$

$$C6 + C7 \text{ conversion: } X_{C6+C7} = \frac{\dot{n}_{convC6,feed} + \dot{n}_{convC7,feed} - \dot{n}_{convC6,prod} - \dot{n}_{convC7,prod}}{\dot{n}_{convC6,feed} + \dot{n}_{convC7,feed}} \quad \text{Eq. 7}$$

In an aspect, the bound zeolite support comprises one or more zeolite powders that are joined together by a binder. The term "zeolite" generally refers to a particular group of crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms is equal to 2. The framework exhibits a negative electrovalence that typically is balanced by the inclusion of cations within the crystal such as metals, alkali metals, alkaline earth metals, or hydrogen. Thus, zeolites are a group of natural or synthetic aluminosilicate minerals that typically contain alkali and alkaline metals. Zeolites are characterized by a framework structure that encloses interconnected cavities occupied by ion-exchangeable large metal cations such as potassium and water molecules permitting reversible dehydration. The actual formula of the zeolite may vary without changing the crystalline structure. In an aspect, the mole ratio of silicon to aluminum (Si/Al) in the zeolite may vary from about 1.0 to about 3.5.

In an aspect, the bound zeolite support comprises a large-pore zeolite. The term "large-pore zeolite" as used herein refers to a zeolite having an effective pore diameter of from about 6 Angstroms (Å) (0.6 nm) to about 15 Å (1.5 nm), alternatively from about 7 Å (0.7 nm) to about 9 Å (0.9 nm). Large pore crystalline zeolites suitable for use in this disclosure include without limitation L-zeolite, X-zeolite, Y-zeolite, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, ZZA-26, SSZ-31, SSZ-33, SSZ-35, SSZ-37, SSZ-41, SSZ-42, SSZ-44, MCM-58, mordenite, faujasite, or combinations thereof. In an aspect, the large pore zeolite has an isotypic framework structure. In an aspect, the bound zeolite support comprises L-zeolite.

L-type zeolite catalysts are a sub-group of zeolitic catalysts. Typical L-type zeolites contain mole ratios of oxides in accordance with the following formula:

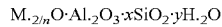

$$M_{2/n}O \cdot Al_2O_3 \cdot xSiO_2 \cdot yH_2O$$

wherein "M" designates at least one exchangeable cation such as barium, calcium, cerium, lithium, magnesium, potassium, sodium, strontium, and zinc as well as non-metallic cations like hydronium and ammonium ions which may be replaced by other exchangeable cations without causing a substantial alteration of the basic crystal structure of the L-type zeolite. The "n" in the formula represents the valence of "M", "x" is 2 or greater; and "y" is the number of water molecules contained in the channels or interconnected voids with the zeolite. L-zeolite, its X-ray diffraction pattern, its properties, and methods for its preparation are described in detail in, U.S. Pat. No. 3,216,789, the content of which is hereby incorporated by reference. In an aspect, the bound zeolite support comprises L-zeolite wherein M is potassium and is hereafter referred to as KL-zeolite.

In an aspect, the catalyst comprises a crystalline zeolite powder, e.g., a KL-zeolite powder, having a mean particle size of less than about 6 microns, alternatively less than about 5 microns, alternatively less than about 4 microns, alternatively less than about 3 microns, or alternatively from about 5 microns to about 2 microns; a median particle size of less than about 5 microns, alternatively less than about 4 microns, alternatively less than about 3 microns, alternatively less than about 2 microns, alternatively from about 5 microns to about 2 microns; or combinations thereof. Zeolites powders having the disclosed mean and median particle sizes may be prepared utilizing any suitable methodology for the preparation of a zeolite. For example, the zeolite may be prepared by techniques such as spray drying or crystallization. In an aspect, the zeolite may then be contacted with other components to form a bound zeolite support.

In an aspect, the binder for use with the zeolite comprises synthetic or naturally occurring zeolites; alumina; clays such as montmorillonite and kaolin; the refractory oxides of metals of Groups IVA and IVB of the Periodic Table of the Elements; oxides of silicon, titanium, zirconium; or combinations thereof. In an aspect, the binder comprises silica. In an aspect, the silica may be in the form of a silica sol. A silica sol may comprise dispersed silica particles in water. The silica sol may be provided in about 20 wt. % to about 30 wt. % aqueous solution having a pH of from about 9.0 to about 10.5 with a viscosity of equal to or less than about 20 mPa·s at 25° C., alternatively from about 1 mPa·s to about 20 mPa·s at 25° C.

Catalyst compositions of this disclosure can include a zeolite support as disclosed herein, a Group VIII metal as disclosed herein on the zeolite support, and at least two halides disclosed herein that are bound to the zeolite support, to the Group VIII metal, or to both the zeolite support and the Group VIII metal. In aspects, the at least two halides are fluoride and a second halide selected from chloride, bromide, or iodide. In further aspects, the at least two halides are fluoride and chloride. In aspects where fluoride is one of the two halides, these catalyst compositions can be referred to as pre-fluorided (Metal)-(Halide)-F catalysts or twice fluorided catalysts because their supports were contacted with a fluorine-containing compound before metal loading, and then contacted with a fluorine-containing compound and another halide-containing compound during metal loading. Specific examples of pre-fluorided (Metal)-(Halide)-F catalysts include pre-fluorided Pt—Cl—F catalysts.

The average crush strength for the catalysts disclosed herein can be calculated. Generally, the average crush strength is calculated by averaging the sample crush strength of at least two samples of the catalyst. Each sample of catalyst comprises a specific number of catalyst pellets, such as 10, 20, 30, 40, 50, 60, 70, 80, 90, or 100 pellets. The sample crush strength can be calculated by averaging the individual pellet crush strength for each pellet in a sample. Each individual pellet crush strength can be measured in accordance with ASTM D4179; alternatively, each individual pellet crush strength can be measured in accordance with ASTM D4179, except the drying step in the standard is performed at 538° C. instead of 400° C.

In some aspects, an average crush strength of the catalyst can be greater than 11.25 lb; alternatively, greater than about 11.79 lb; alternatively, greater than about 12.00 lb; alternatively, greater than about 13.00 lb; alternatively, greater than about 13.20 lb; alternatively, greater than about 13.40 lb. In some additional aspects, the average crush strength can be less than about 15.00 lb; alternatively, less than about 14.00 lb; alternatively, less than about 13.90 lb; alternatively, less than about 13.70 lb; alternatively, less than about 13.50 lb.

In some aspects, a sample crush strength of the catalyst can be greater than 11.91 lb; alternatively, greater than about 12.00 lb; alternatively, greater than about 13.00 lb; alternatively, greater than about 13.10 lb. In some additional aspects, the sample crush strength of the catalyst can be less than about 15.00 lb; alternatively, less than about 14.00 lb; alternatively, less than about 13.90 lb; alternatively, less than about 13.80 lb; alternatively, less than about 13.70 lb.

In some aspects, an average crush strength per length of extrudate (e.g., pellet) of the catalyst can be greater than 2.25 lb/mm; alternatively, greater than 2.48 lb/mm; alternatively, greater than about 2.50 lb/mm; alternatively, greater than about 2.60 lb/mm; alternatively, greater than about 2.70 lb/mm; alternatively, greater than about 2.80 lb/mm; alternatively, greater than about 2.90 lb/mm; alternatively, greater than about 3.00 lb/mm. In some additional aspects, the average crush strength per length of extrudate of the catalyst can be less than about 3.50 lb/mm; alternatively, less than about 3.40 lb/mm; alternatively, less than about 3.30 lb/mm; alternatively, less than about 3.20 lb/mm; alternatively, less than about 3.10 lb/mm.

In some aspects, a sample crush strength per length of extrudate of the catalyst can be greater than 2.65 lb/mm; alternatively, greater than about 2.70 lb/mm. In some additional aspects, the sample crush strength per length of extrudate of the catalyst can be less than about 3.50 lb/mm; alternatively, less than about 3.40 lb/mm; alternatively, less than about 3.30 lb/mm.

In some aspects, less than 22% of the pellets of the catalyst that are measured in accordance with ASTM D4179 have an individual pellet crush strength of less than 10 lb/pellet; alternatively, less than 21% of the pellets that are measured in accordance with ASTM D4179 have an individual pellet crush strength of less than 10 lb/pellet.

In some aspects, equal to or less than 14% of the pellets of the catalyst that are measured in accordance with ASTM D4179 have an individual pellet crush strength of less than 9 lb/pellet; alternatively, less than 13% of the pellets that are measured in accordance with ASTM D4179 have an individual pellet crush strength of less than 9 lb/pellet.

In an aspect, a method for the preparation of a catalyst comprises blending a zeolite of the type disclosed herein, a binder of the type disclosed herein, and water to form a paste and shaping the paste into a wet extruded base or extrudate. In an aspect, the wet extruded base may have any suitable shape. Any suitable shaping process or technology may be employed and may include without limitation, extrusion, spray drying, pelletizing, agglomeration and the like. In an aspect, shaping the paste into a wet extruded base or extrudate, for example, is described in U.S. Pat. Nos. 8,263,518, 7,902,105, 6,190,539, and 5,558,851 each of which are incorporated by reference herein in their entirety.

The zeolite and binder (e.g., silica) may be combined to give a weight ratio of from about 95:5 to about 50:50 zeolite:binder; alternatively from about 90:10 to about 70:30 zeolite:binder; or alternatively from about 88:12 to about 78:22 zeolite:binder in the bound zeolite support. The amount of water necessary to form an extrudable paste may be determined by one of ordinary skill in the art. The amount of water may be sufficient to form a paste having a dough-like consistency. Such a paste may be characterized by a resistance to crumbling (i.e., not brittle) and the ability to maintain a cohesive form (i.e., not a soup-like consistency). The paste may be further characterized by an ability to form a plug at a die interface of an extruder, which may then be expelled out through the die openings in a cylindrical shape form resembling spaghetti strands, which may be cut or chopped into cylinders or pellets having desired dimensions and being either solid or hollow.

In an aspect, the paste further comprises an extrusion aid. An extrusion aid may function to improve the rheology of the paste. This improvement in the rheology of the paste may function to improve flow of the paste in the shaping process (e.g. through the extrusion die). Improved flow in the shaping process leads to easier equipment start-up, smoother extrusion, faster processing, lower extrusion pressures, and improved product appearance. In an aspect, the extrusion aid comprises cellulose-based materials, ethylene glycol, stearic acid, or combinations thereof. In an aspect, the extrusion aid comprises a cellulose ether such as methylcellulose, carboxymethylcellulose, ethylhydroxyethylcellulose, hydroxyethylcellulose, hydroxypropylcellulose, methylhydroxyethylcellulose, methylhydroxypropylcellulose, or combinations thereof. An example of an extrusion aid suitable for use in this disclosure includes without limitation METHOCEL®, a cellulose based material commercially available from Dow Chemical Company. Extrusion aids, their effective amounts and methods of incorporation into a catalyst base composition may be varied and selected as needed to meet some user and/or process objective. Hereafter, the shaped paste exiting a die and of desired dimensions will be referred to as the "wet extruded base" (WEB).

Excess water in the wet extruded base may be removed by drying to form an extruded base (EB) prior to further processing. Any suitable method for drying wet solids may be used to dry the WEB, and may include, for example drying in air or an inert gas such as nitrogen or argon. Drying temperatures may range from about 200° F. (93.3° C.) to about 400° F. (204° C.), alternatively from about 200° F. (93.3° C.) to about 300° F. (149° C.), or alternatively from about 225° F. (107° C.) to about 275° F. (135° C.). Drying times may range from equal to or greater than about 1 hour, alternatively from about 1 hour to about 10 hours, or alternatively from about 2 hours to about 5 hours.

In an aspect, the WEB or EB may be contacted with a fluorine-containing compound in a process generally referred to as fluoridation. The fluorine-containing compound may be in the solid phase, liquid phase, gas phase, or combinations thereof.

Examples of fluorine-containing compounds suitable for use in this disclosure include without limitation tetramethylammonium fluoride (TMAF), ammonium fluoride ($NH_4F$ or AF), or combinations thereof.

In some aspects, the fluorine-containing compound may be an organic ammonium halide compound and may comprise one or more compounds represented by the general formula $N(R)_4F$, where R represents a hydrogen or a substituted or unsubstituted carbon chain molecule having from 1 to 20 carbon atoms wherein each R may be the same or different. In an aspect, R is methyl, ethyl, propyl, butyl, or combinations thereof. Alternatively, R is methyl. Examples of suitable organic ammonium fluoride compounds include without limitation ammonium fluoride, tetramethylammonium fluoride, tetraethylammonium fluoride, tetrapropylammonium fluoride, tetrabutylammonium fluoride, methyltriethylammonium fluoride, or combinations thereof.

The organic ammonium halide compound may also comprise at least one hydrofluoric acid and at least one ammonium hydroxide represented by the formula $N(R')_4OH$, where R' is hydrogen or a substituted or unsubstituted carbon chain molecule having from 1 to 20 carbon atoms wherein each R' may be the same or different. In an aspect, R' is methyl, ethyl, propyl, butyl, or combinations thereof. Alternatively, R is methyl. Examples of organic ammonium hydroxides suitable for use in this disclosure include tetraalkylammonium hydroxides such as tetramethylammonium hydroxide, tetraethylammonium hydroxide, tetrapropylammonium hydroxide, tetrabutylammonium hydroxide, or combinations thereof.

In an aspect, the WEB is contacted with a fluorine-containing compound of the type disclosed herein to form a fluorinated washed extruded base (F-WEB). In an alternative aspect, the EB is contacted with a fluorine-containing compound of the type disclosed herein to form a fluorinated extruded base (F-EB).

In an aspect, neither the WEB nor EB is contacted with a fluorine-containing compound. In such aspects, the extruded base (EB) may be calcined to form a calcined extruded base (CEB). Calcination temperatures may range of from about 500° F. (260° C.) to about 1500° F. (816° C.), alternatively from about 700° F. (371° C.) to about 1100° F. (593° C.), or alternatively from about 850° F. (454° C.) to about 1100° F.

(593° C.). Calcination times may range from about 0.5 to about 5 hours, or alternatively from about 0.5 to about 1.5 hours. In such aspects, the calcination may be carried out in an oxygen-containing atmosphere having a flow rate of from about 10 cubic feet per hour (CFH) (4.7 L/min) to about 20 CFH (9.4 L/min), alternatively the calcination may be carried out in air at a flow rate of from about 10 CFH (4.7 L/min) to about 20 CFH (9.4 L/min), or alternatively, the calcination may be carried out in "dry" air having a flow rate of about 10 CFH (4.7 L/min) to about 20 CFH (9.4 L/min). Herein dry air refers to air having a dew point of less than about −40° F. (−40° C.). In an aspect, the CEB may be contacted with a fluorine-containing compound of the type disclosed herein and result in a fluorinated calcined extruded base, (F-CEB).

In an aspect, the extruded base is calcined (in the absence of a preceding drying step as described previously) to form a calcined extruded base (CEB). Calcination temperatures may range of from about 500° F. (260° C.) to about 1500° F. (816° C.), alternatively from about 700° F. (371° C.) to about 1100° F. (593° C.), or alternatively from about 850° F. (454° C.) to about 1100° F. (593° C.). Calcination times may range from about 0.5 to about 5 hours, or alternatively from about 0.5 to about 1.5 hours. In such aspects, the calcination may be carried out in an oxygen-containing atmosphere having a flow rate of from about 10 cubic feet per hour (CFH) (4.7 L/min) to about 20 CFH (9.4 L/min), alternatively the calcination may be carried out in air at a flow rate of from about 10 CFH (4.7 L/min) to about 20 CFH (9.4 L/min), alternatively, the calcination may be carried out in "dry" air having a flow rate of about 10 CFH (4.7 L/min) to about 20 CFH (9.4 L/min). Herein dry air refers to air having a dew point of less than about −40° F. (−40° C.). In an aspect, the CEB may be contacted with a fluorine-containing compound of the type disclosed herein and result in a fluorinated calcined extruded base, (F-CEB).

In an aspect, the CEB may be washed to form a washed CEB ("WCEB"). Washing the CEB may reduce the amount of "readily removable" alkali that may be present. The term washing, as used herein, is meant to include any process where liquid (e.g. water) in excess of the material's pore volume is contacted with the CEB. The "readily removable" alkali is defined herein as the alkali that may be washed out of the CEB after 5 washings by contacting an about 1:1 volume of liquid to weight of extrudate at ambient temperature. Several washings may be necessary in order to substantially reduce the amount of readily removable alkali. In some aspects, the CEB may be subjected to at least 5 washings in order to remove a substantial amount of the readily removable alkali. In an aspect, the wash water is distilled or deionized water having a pH of from about 5 to about 9. The washing temperature may range from about 70° F. (21° C.) to about 200° F. (93.3° C.), alternatively of from about 80° F. (27° C.) to about 130° F. (54° C.), alternatively from about 90° F. (32° C.) to about 110° F. (43° C.). The washing time may range from about 5 to about 60 minutes per wash, alternatively from about 15 to about 30 minutes per wash.

After washing to reduce the amount of readily removable alkali, the washed WCEB may be dried to form a washed and dried CEB. The drying temperature may range from about 200° F. (93.3° C.) to about 400° F. (204° C.), alternatively from about 200° F. (93.3° C.) to about 300° F. (149° C.), or alternatively from about 225° F. (107° C.) to about 275° F. (135° C.). The drying time may range from at least about 1 hour, alternatively from about 1 to about 10 hours, or alternatively from about 2 to about 5 hours.

The washed and dried CEB may be calcined to form a washed, dried, and calcined CEB. The calcining temperature may range from about 500° F. (260° C.) to about 1200° F. (649° C.), alternatively from about 700° F. (371° C.) to about 1100° F. (593° C.), or alternatively from about 850° F. (454° C.) to about 1000° F. (593° C.). The calcining time may range from about 0.5 to about 5.0 hours, or alternatively from about 0.5 to about 1.5 hours. In such aspects the calcination may be carried out in an oxygen containing atmosphere having a flow rate of from about 10 CFH (4.7 L/min) to about 20 CFH (9.4 L/min), alternatively the calcination may be carried out in air at a flow rate of from about 10 CFH (4.7 L/min) to about 20 CFH (9.4 L/min), or alternatively, the calcination may be carried out in "dry" air having an flow rate of about 10 CFH (4.7 L/min) to about 20 CFH (9.4 L/min).

The F-WEB, F-EB, F-CEB, and/or F-WCEB may be collectively referred to as fluorinated base materials (FBMs). In an aspect, a method of preparing an aromatization catalyst comprises contacting at least one of the WEB, EB, CEB, or WCEB thereof with a fluorine-containing compound to yield one or more FBMs. In an aspect, the fluorine-containing compound may be contacted with at least two of the WEB, EB, CEB, or WCEB to yield one or more FBMs. In an aspect, the fluorine-containing compound may be contacted with any combination of the WEB, EB, CEB, and/or WCEB to yield one or more FBMs. In an aspect, contact of the WEB, EB, CEB and/or WCEB with the fluorine-containing compound to produce a FBM occurs in the temperature range of from about 20° C. to about 100° C., alternatively from about 22° C. to about 80° C., or alternatively from about 25° C. to about 50° C.

It is to be understood that contact of the fluorine-containing compound results in fluoride being associated with the subsequent materials formed during preparation of an aromatization catalyst. For example, fluorination of the WEB results in an F-WEB, which may then be dried to yield an F-EB, which may be calcined to yield an F-CEB. Similarly, fluorination of the EB results in an F-EB, which may be calcined to yield an F-CEB. As noted previously, each of these FBMs may be further washed, dried, and calcined. Consequently, when the wet extruded base is fluorinated, a fluorinated wet extruded base is formed and subsequently a fluorinated extruded base, a calcined fluorinated extruded base, a washed calcined fluorinated extruded base, a dried washed calcined fluorinated extruded base, and so forth. In aspects where the extruded base is contacted with a fluorine-containing compound a fluorinated extruded base is formed and subsequently a calcined fluorinated extruded base, a washed calcined fluorinated extruded base, a dried washed calcined fluorinated extruded base, and so forth. In aspects where the calcined extruded based is contacted with a fluorine-containing compound a fluorinated calcined extruded base is formed and subsequently a washed fluorinated calcined extruded base, a dried washed fluorinated calcined extruded base, and so forth. Again, any of the resultant FEB, F-EB, F-CEB, or F-WCEB may be collectively referred to as fluorinated base materials (FBMs).

The FBMs may be subjected to further processing steps to yield a bound zeolite supports and/or catalysts (e.g., aromatization catalysts) as described herein. For example, an FBM may be further washed, dried, and calcined to form a bound zeolite support (which may also be referred to as a catalyst support, catalyst precursor, precursor support, support material, or the like, each of which indicating that one or more catalytic materials have not yet been added to the support).

In an aspect, the FBM may be washed to form a washed FBM. The term washing, as used herein, is meant to include any process where liquid (e.g. water) in excess of the material's pore volume is contacted with the FBM. Several washings may be performed. In some aspects, the FBM may be subjected to from 1 to 5 washings. In an aspect, the wash water is distilled or deionized water having a pH of from about 5 to about 9. The washing temperature may range from about 70° F. (21° C.) to about 200° F. (93.3° C.), alternatively of from about 80° F. (27° C.) to about 130° F. (54° C.), alternatively from about 90° F. (32° C.) to about 110° F. (43° C.). The washing time may range from about 5 to about 60 minutes per wash, alternatively from about 15 to about 30 minutes per wash.

In an aspect, potassium ions ($K^+$) may be incorporated in the wash liquid (e.g., water) to neutralize any protonic sites that may have formed during washing and/or to prevent the formation of protonic sites. Any suitable K-containing compound soluble in water may be used including, but not limiting, KOH, $KNO_3$, $KHCO_3$, $K_2CO_3$, K-acetate, K-salts of common organic acids such as oxalic, citric, acetic, propionic, and the like. The $K^+$ may be present in amounts of ranging from about 100 to about 1000 ppm. Protonic or Brønsted acid sites may result in acidic properties with adverse effect on the catalyst activity and/or deactivation rate. In an aspect, the fluorine-containing compound is contacted with the CEB prior to washing.

After washing, the washed FBM may be dried to form a washed and dried FBM. The drying temperature may range from about 200° F. (93.3° C.) to about 400° F. (204° C.), alternatively from about 200° F. (93.3° C.) to about 300° F. (149° C.), alternatively from about 225° F. (107° C.) to about 275° F. (135° C.). The drying time may range from at least about 1 hour, alternatively from about 1 to about 10 hours, or alternatively from about 2 to about 5 hours.

The washed and dried FBM may be calcined to form a washed, dried, and calcined FBM. The calcining temperature may range from about 500° F. (260° C.) to about 1200° F. (649° C.), alternatively from about 700° F. (371° C.) to about 1100° F. (593° C.), or alternatively from about 850° F. (454° C.) to about 1000° F. (593° C.). The calcining time may range from about 0.5 to about 5.0 hours, or alternatively from about 0.5 to about 1.5 hours. In such aspects, the calcination may be carried out in an oxygen containing atmosphere having a flow rate of from about 10 CFH (4.7 L/min) to about 20 CFH (9.4 L/min), alternatively the calcination may be carried out in air at a flow rate of from about 10 CFH (4.7 L/min) to about 20 CFH (9.4 L/min), alternatively, the calcination may be carried out in "dry" air having an flow rate of about 10 CFH (4.7 L/min) to about 20 CFH (9.4 L/min).

In an aspect, the washed, dried, and calcined FBM may be referred to as a bound zeolite support and may be used as a support material to prepare an aromatization catalyst having one or more catalytic materials deposited thereon. In an aspect, the bound zeolite support comprises fluoride present in an amount of from about 0.1 wt. % to about 5 wt. %, alternatively from about 0.1 wt. % to about 3 wt. %, alternatively from about 0.3 wt. % to about 1.8 wt. % as determined using any suitable methodology such as x-ray fluorescence.

The method for preparation of an aromatization catalyst may further comprise impregnating the bound zeolite support with one or more catalytic compounds such as a Group VIII metal (e.g., platinum) and one or more halides (e.g., chloride).

The bound zeolite support having been prepared as previously disclosed herein may be further processed to incorporate one or more catalytic materials. In an aspect, the addition of a metal and chloride to the bound zeolite support forms a catalyst capable of catalyzing reactions such as the conversion of hydrocarbons to aromatics.

In an aspect, one or more Group VIII metals are added to the bound zeolite support to form a metalized catalyst support. The metal may be added to the bound zeolite support by employing any suitable methodology, e.g., ion-exchange, incipient wetness impregnation, or pore fill impregnation. In an aspect, the metal is added to the bound zeolite support by impregnation with a metal-containing solution. The metal in the metal-containing solution may be at least one Group VIII metal; alternatively, Pt, Pd, Rh, Ir, Ru, Os, or combinations thereof; alternatively, platinum.

In an aspect, the metal comprises platinum that is added to the bound zeolite support via contact with a metal-containing solution containing at least one platinum-containing compound. Examples of suitable platinum-containing compounds for contact with the bound zeolite support include without limitation platinum compounds that form positively charged platinum complex ions in solution such as for example platinum salts such as chlorides and nitrates; platinum complexes with ammines; or combinations thereof. For example, the platinum-containing compound may be any decomposable platinum-containing compound including, but not limited to, ammonium tetrachloroplatinate, chloroplatinic acid, diammineplatinum (II) nitrite, bis-(ethylenediamine)platinum (II) chloride, platinum (II) acetylacetonate, dichlorodiammine platinum, platinum (II) chloride, tetraammineplatinum (II) hydroxide, tetraammineplatinum chloride, and tetraammineplatinum (II) nitrate. In an aspect, the platinum source is tetraammine platinum chloride (TAPC). The amount of platinum in the metalized catalyst support may range from about 0.1 to about 5 wt. %, alternatively from about 0.1 to about 3 wt. %, alternatively from about 0.3 to about 1.8 wt. %.

In an aspect, one or more halides are added to the bound zeolite support by contact with a halide-containing compound to form a halided catalyst support. The one or more halides may be added into the bound zeolite support separately; alternatively, the one or more halides may be added to the bound zeolite support at the same time. Such halides may also be incorporated during addition of a metal, alternatively the one or more halides are incorporated in a separate step that may be pre- or post-addition of the metal, to form a halided, metalized catalyst support. Examples of suitable halides include without limitation chloride, fluoride, bromide, iodide, or combinations thereof. Such halides may be introduced as the organic ammonium halide compound.

The organic ammonium halide compound may comprise one or more compounds represented by the formula $N(R)_4X$, where X is a halide and where R represents a hydrogen or a substituted or unsubstituted carbon chain molecule having 1-20 carbons wherein each R may be the same or different. In an aspect, R is selected from the group consisting of methyl, ethyl, propyl, butyl, and combinations thereof, more specifically methyl. In an aspect, the halide is chloride and is added to the bound zeolite support by contact with a chlorine-containing compound.

Suitable chlorine-containing compounds may be organic ammonium chloride compounds and may comprise one or more compounds represented by the general formula $N(R)_4Cl$, where R represents a hydrogen or a substituted or unsubstituted carbon chain molecule having from 1 to 20 carbon atoms wherein each R may be the same or different.

In an aspect, R is methyl, ethyl, propyl, butyl, or combinations thereof. Alternatively, R is methyl. Examples of suitable organic ammonium chloride compounds include without limitation ammonium chloride, tetramethylammonium chloride, tetraethylammonium chloride, tetrapropylammonium chloride, tetrabutylammonium chloride, methyltriethylammonium chloride, or combinations thereof.

In an aspect, the halided metalized catalyst support comprises chloride present in an amount of from about 0.1 wt. % to about 5 wt. %, alternatively from about 0.1 wt. % to about 3 wt. %, or alternatively from about 0.3 wt. % to about 1.8 wt. %. In an aspect, the halided metalized catalyst support comprises both chloride and fluoride, which may be present in a Cl:F ratio of from about 1:10 to 10:1, alternatively from about 1:5 to 5:1, or alternatively from about 1:2 to 2:1.

In an aspect, the halided metalized catalyst support is allowed to set for several hours prior to additional processing. In an aspect, the halided metalized catalyst support is allowed to set for about 1 to about 24 hours, alternatively for about 2 to about 8 hours, or alternatively for about 3 to about 6 hours. In an aspect, the catalyst comprises a metalized, halided support.

Following impregnation of the bound zeolite support with a metal and one or more halides to form a halided metalized catalyst support, the halided metalized catalyst support may then be further processed as described herein. The halided metalized catalyst support may be processed to remove undesirable compounds remaining from the impregnation steps, for example by drying to remove compounds and/or heating to decompose compounds. In an aspect, the halided metalized catalyst support is dried and calcined as described as follows.

The halided metalized catalyst support may be dried to form a dried halided metalized catalyst support. The drying temperature may ranging from about 100° F. (38° C.) to about 300° F. (149° C.), alternatively from about 150° F. (66° C.) to about 250° F. (121° C.), or alternatively from about 200° F. (93.3° C.) to about 220° F. (104° C.). The drying time may range from about 0.1 to about 6 hours, alternatively for from about 0.2 to about 4 hours, or alternatively for from about 0.2 to about 3 hours. The halided metalized catalyst support may be dried using any suitable equipment for drying under the disclosed conditions. For example, the halided metalized catalyst support may be dried using rotary evaporation techniques at temperatures greater than about 100° F. (38° C.), under a pressure of about 30 inches of mercury (102 kPa).

The dried halided metalized catalyst support may be calcined to form a dried and calcined halided metalized catalyst support. The calcining temperature may range from about 400° F. (204° C.) to about 900° F. (282° C.), alternatively from about 500° F. (260° C.) to about 700° F. (371° C.), or alternatively from about 550° F. (288° C.) to about 600° F. (316° C.). The calcining time may range from about 0.5 to about 5 hours, or alternatively from about 0.5 to about 2.5 hours. The calcination may be carried out in an oxygen containing atmosphere under a flow rate of from about 5 CFH (2.4 L/min) to about 20 CFH (9.4 L/min). Alternatively, the calcination may be carried out in air using a flow rate of from about 5 CFH (2.4 L/min) to about 20 CFH (9.4 L/min), alternatively in dry air using a flow rate of about 5 CFH (2.4 L/min) to about 20 CFH (9.4 L/min). Upon completion of processing the halided metalized catalyst support (e.g., washing, drying, and calcining), the resultant processed halided metalized catalyst support may be referred to as a catalyst (e.g., aromatization catalyst) and employed in a suitable chemical reaction and process.

Particular processes are now discussed for preparing a catalyst.

In an aspect, a method for preparing a catalyst may include blending a zeolite of the type disclosed herein, a binder of the type disclosed herein, and water to form a paste and shaping the paste into a wet extruded base (WEB) or extrudate. The WEB may have excess water removed therefrom or otherwise dried to form a dried extruded base (EB). After removing excess water or drying, the method may include contacting the EB with a fluorine-containing compound to form a fluorinated dried extruded base (F-EB). The F-EB may then be calcined to form a fluorinated calcined extruded base (F-CEB). The F-CEB can then be washed, dried, and again calcined to form a bound zeolite support. The bound zeolite support can then be contacted with a metal disclosed herein and a chlorine containing compound disclosed herein, then dried, and then again calcined to form the catalyst. In an aspect, the F-EB may be dried before calcining the F-EB to form the F-CEB.

In another aspect, a method for preparing a catalyst may include blending a zeolite of the type disclosed herein, a binder of the type disclosed herein, and water to form a paste and shaping the paste into a wet extruded base (WEB) or extrudate. The WEB may have excess water removed therefrom or otherwise dried to form a dried extruded base (EB). The EB may then be calcined to form a calcined extruded base (CEB). The CEB can then be contacted with a fluorine-containing compound to form a fluorinated calcined extruded base (F-CEB). The F-CEB can then be washed, dried, and calcined to form a bound zeolite support. The bound zeolite support can then be contacted with a metal disclosed herein and a chlorine containing compound disclosed herein, then dried, and then again calcined to form the catalyst. In an aspect, the F-CEB may be dried and/or calcined before washing, drying, and then being calcined.

In another aspect, a method for preparing a catalyst may include blending a zeolite of the type disclosed herein, a binder of the type disclosed herein, and water to form a paste and shaping the paste into a wet extruded base (WEB) or extrudate. The WEB may have excess water removed therefrom or otherwise dried to form a dried extruded base (EB). The EB may then be calcined to form a calcined extruded base (CEB). The CEB can then be washed, dried, and again calcined to form a twice calcined extruded based (2CEB). The 2CEB can then be contacted with a fluorine-containing compound to form a bound zeolite support. The bound zeolite support can then be contacted with a metal disclosed herein and a chlorine containing compound disclosed herein, then dried, and then again calcined to form the catalyst.

In an aspect, a method for preparing a catalyst may include blending a zeolite of the type disclosed herein, a binder of the type disclosed herein, and water to form a paste and shaping the paste into a wet extruded base (WEB) or extrudate. The WEB may have excess water removed therefrom or otherwise dried to form a dried extruded base (EB). After removing excess water or drying, the method may include contacting the EB with a first fluorine-containing compound to form a fluorinated dried extruded base (F-EB). The F-EB may then be calcined to form a fluorinated calcined extruded base (F-CEB). The F-CEB can then be washed, dried, and again calcined to form a bound zeolite support. The bound zeolite support can then be contacted with a metal disclosed herein, a chlorine containing compound disclosed herein, and a second fluorine-containing compound disclosed herein, then dried, and then again calcined to form the catalyst. In an aspect, the F-EB may be dried before calcining the F-EB to form the F-CEB.

In another aspect, a method for preparing a catalyst may include blending a zeolite of the type disclosed herein, a binder of the type disclosed herein, and water to form a paste and shaping the paste into a wet extruded base (WEB) or extrudate. The WEB may have excess water removed therefrom or otherwise dried to form a dried extruded base (EB). The EB may then be calcined to form a calcined extruded base (CEB). The CEB can then be contacted with a first fluorine-containing compound to form a fluorinated calcined extruded base (F-CEB). The F-CEB can then be washed, dried, and again calcined to form a bound zeolite support. The bound zeolite support can then be contacted with a metal disclosed herein, a chlorine containing compound disclosed herein, and a second fluorine-containing compound disclosed herein, then dried, and then again calcined to form the catalyst. In an aspect, the F-CEB may be dried and/or calcined before washing, drying, and then calcining the F-CEB to form the bound zeolite support.

In another aspect, a method for preparing a catalyst may include blending a zeolite of the type disclosed herein, a binder of the type disclosed herein, and water to form a paste and shaping the paste into a wet extruded base (WEB) or extrudate. The WEB may have excess water removed therefrom or otherwise dried to form a dried extruded base (EB). The EB may then be calcined to form a calcined extruded base (CEB). The CEB can then be washed, dried, and again calcined to form a twice calcined extruded based (2CEB). The 2CEB can then be contacted with a first fluorine-containing compound and then dried and/or calcined to form a bound zeolite support. The bound zeolite support can then be contacted with a metal disclosed herein, a chlorine containing compound disclosed herein, and a second fluorine-containing compound disclosed herein, then dried, and then again calcined to form the catalyst.

In an aspect, the catalyst prepared as disclosed herein is used as a catalyst in an aromatization reactor system comprising at least one aromatization reactor and its corresponding processing equipment. As used herein, the terms "aromatization," "aromatizing" and "reforming" refer to the treatment of a hydrocarbon feed to provide an aromatics enriched product, which in one aspect is a product whose aromatics content is greater than that of the feed. Typically, one or more components of the feed undergo one or more reforming reactions to produce aromatics. Some of the hydrocarbon reactions that occur during the aromatization operation include the dehydrogenation of cyclohexanes to aromatics, dehydroisomerization of alkylcyclopentanes to aromatics, dehydrocyclization of acyclic hydrocarbons to aromatics, or combinations thereof. A number of other reactions also occur, including the dealkylation of alkylbenzenes, isomerization of paraffins, hydrocracking reactions that produce light gaseous hydrocarbons, e.g., methane, ethane, propane and butane, or combinations thereof.

The aromatization reaction occurs under process conditions that thermodynamically favor the dehydrocyclization reaction and limit undesirable hydrocracking reactions. The pressures may be from about 0 pounds per square inch gauge (psig) (0 kPa) to about 500 psig (3447 kPa), or alternatively from about 25 psig (172 kPa) to about 300 psig (2068 kPa). The molar ratio of hydrogen to hydrocarbons may be from about 0.1:1 to about 20:1, alternatively from about 1:1 to about 6:1. The operating temperatures include reactor inlet temperatures from about 700° F. (371° C.) to about 1050° F. (566° C.), or alternatively from about 900° F. (482° C.) to about 1000° F. (538° C.). The liquid hourly space velocity for the hydrocarbon feed over the aromatization catalyst may be from about 0.1 $hr^{-1}$ to about 10 $hr^{-1}$, or alternatively from about 0.5 $hr^{-1}$ to about 2.5 $hr^{-1}$.

The composition of the feed is a consideration when designing catalytic aromatization systems. In an aspect, the hydrocarbon feed comprises non-aromatic hydrocarbons containing at least six carbon atoms. The feed to the aromatization system is a mixture of hydrocarbons comprising $C_6$ to $C_8$ hydrocarbons containing up to about 10 wt. % and alternatively up to about 15 wt. % of $C_5$ and lighter hydrocarbons ($C_5^-$) and containing up to about 10 wt. % of $C_9$ and heavier hydrocarbons ($C_9^+$). Such low levels of $C_9+$ and $C_5^-$ hydrocarbons maximize the yield of high value aromatics. In some aspects, an optimal hydrocarbon feed maximizes the percentage of $C_6$ hydrocarbons. Such a feed may be achieved by separating a hydrocarbon feedstock such as a full range naphtha into a light hydrocarbon feed fraction and a heavy hydrocarbon feed fraction, and using the light fraction.

In another aspect, the feed is a naphtha feed. The naphtha feed may be a light hydrocarbon, with a boiling range of about 70° F. (21° C.) to about 450° F. (232° C.). The naphtha feed may contain aliphatic, naphthenic, or paraffinic hydrocarbons. These aliphatic and naphthenic hydrocarbons are converted, at least in part, to aromatics in the aromatization reactor system. While catalytic aromatization typically refers to the conversion of naphtha, other feedstocks may be treated as well to provide an aromatics enriched product. Therefore, while the conversion of naphtha is one aspect, the present disclosure may be useful for activating catalysts for the conversion or aromatization of a variety of feedstocks such as paraffinic hydrocarbons, olefinic hydrocarbons, acetylenic hydrocarbons, cyclic paraffin hydrocarbons, cyclic olefin hydrocarbons, and mixtures thereof, and particularly saturated hydrocarbons.

In an aspect, the feedstock is substantially free of sulfur, nitrogen, metals, and other known poisons for aromatization catalysts. In an aspect, the feedstock contains less than about 100 ppb of sulfur. If present, such poisons may be removed using any suitable methodology. In some aspects, the feed may be purified by first using conventional hydrofining techniques, then using sorbents to remove the remaining poisons.

In an aspect, aromatization catalysts of the type disclosed herein display improved catalyst selectivity as determined by the ratio of benzene to toluene produced when using a naphtha feed. In such aspects, the selectivity may range from about 10% to about 100%, alternatively from about 20% to about 90%, or alternatively from about 30% to about 80%.

EXAMPLES

The present subject matter will be described in greater detail by way of specific examples. The following examples are offered for illustrative purposes only, and are not intended to limit the invention in any manner. Those of skill in the art will readily recognize a variety of noncritical parameters which may be changed or modified to yield essentially the same results.

Support Examples

Support A was a dried silica bound KL-Zeolite extruded base containing about 80 wt. % KL-Zeolite. A mixture was prepared from about 609 grams (g) of crystalline KL-zeolite powder and about 30 g of methyl cellulose. This mixture was thoroughly blended in a muller. To this mixture, about 714 g of an about 20 wt. % aqueous solution of silica (SI-350, obtained from CCIC (Japan)) was added and thoroughly blended. To accomplish thorough blending, the silica sol was added to the muller over an about 11 minute period. After the silica sol was added to the mixture, water was added to bring the moisture to a level of about 35 wt. % to about 40 wt. % loss on ignition (LOI) for extrusion. Loss on ignition is the percentage of weight lost when a sample is heated at about 1000° F. (538° C.) for about 1 hour in dry air. The mixture was then extruded through a 1/16 inch (1.6 mm) die. The extrudates were then dried at about 250° F. (121° C.) for about 4 hours to give Support A, an extruded base ("EB").

Support A was then calcined for about 1 hour at about 900° F. (482° C.) to give Support B, a calcined extruded base ("CEB"). During the calcination the temperature was ramped at 300° F./hr to the final 900° F. (482° C.) setpoint and a 10 SCFH (4.7 L/min) airflow was maintained through the particle bed.

Support C was a washed calcined extruded base ("WCEB"). An about 100 g portion of the calcined extruded base (Support B) was washed with about 250 mL of about 100° F. (37.8° C.). deionized water. This wash time was sufficient to achieve good contacting of the solids and liquids. This washing was repeated for a total of three washings. The washed extrudate was then dried for about 4 hours at about 250° F. (121° C.) and then calcined in air at about 900° F. (482° C.) for about 1 hour in flowing dry air.

Fluorided Support 1 was prepared by contacting 12 grams of Support A with 2.33 grams of a 20 wt. % solution of tetramethylammonium fluoride (TMAF) using incipient wetness techniques. The support was allowed to rest for 16 hours and then dried at 150° C. for 2 hours followed by a two hour temperature ramp to 500° C., then holding at 500° C. for 1 hour.

Fluorided Support 2 was prepared by contacting 11 grams of Support B with a mixture of 2.33 grams of a 20 wt. % solution of tetramethylammonium fluoride (TMAF) and 1.67 grams of water, using incipient wetness techniques. The support was allowed to rest for 16 hours and then dried at 150° C. for 2 hours followed by a two hour temperature ramp to 500° C., then holding at 500° C. for 1 hour.

Fluorided Supports 3-7 were prepared by contacting 64.36 grams of Support C with a mixture of about 15 grams of a 20 wt. % solution of tetramethylammonium fluoride (TMAF) and about 15 grams of water, using incipient wetness techniques. The support was allowed to rest for 4 hours. The support was then divided into four portions, with each portion separately dried at 150° C. for 2 hours followed by a temperature ramp to a final hold temperature for six hours. The treatment temperatures used to produce fluorided supports 3-7 are listed in Table 1. Analysis of these fluorided base materials is summarized in Table 2.

TABLE 1

Treatment temperatures for fluorided supports 3-7 (FBMs)

| Fluorided Support | Temperature ramp time | Final hold temperature |
|---|---|---|
| 3 | 7 hours | 500° C. |
| 4 | 6 hours | 450° C. |
| 5 | 5 hours | 400° C. |
| 6 | 4 hours | 350° C. |
| 7 | 4 hours | 350° C. |

TABLE 2

Analysis of Fluorided Supports (FBMs)

| | | | | Fluorided Base-KL Microporosity | | |
|---|---|---|---|---|---|---|
| Support Example | Support Description | F-Support Example | Treatment Temp. (° C.) | Surface Area ($m^2/g$) | Pore Volume (cc/g) | Micropore volume (cc/g) |
| C | WCEB | Untreated | — | 215 | 0.225 | 0.077 |
| A | EB | 1 | 500 | 125 | 0.207 | 0.047 |
| B | CEB | 2 | 500 | 105 | 0.185 | 0.038 |
| C | WCEB | 7 | 350 | 121 | 0.128 | 0.048 |
| C | WCEB | 6 | 350 | 99 | 0.160 | 0.040 |
| C | WCEB | 5 | 400 | 188 | 0.186 | 0.072 |
| C | WCEB | 4 | 450 | 109 | 0.134 | 0.043 |
| C | WCEB | 3 | 500 | 161 | 0.178 | 0.063 |

Catalyst Examples

Platinum-impregnated KL-zeolite catalysts were prepared from in the following manner. An impregnating mixture of about 0.18 g tetraammineplatinum (II) chloride (TAPC), about 0.36 g of a 50 wt. % aqueous solution of tetramethylammonium chloride (TMAC), and about 3.5 g water was formed and added to a container containing about 10 g of the bound zeolite support (either EB, CEB, or WCEB), using incipient wetness techniques. The impregnated bound zeolite support was then allowed to stand for about 16 hours at room temperature. The impregnated bound zeolite support was dried in a vacuum for about 4 hours at about 85° C. The resulting material was then calcined ramping to an initial hold temperature of about 150° C. for about 2 hours, then the temperature was ramped over about 4 hours to a second hold temperature of about 350° C. for 6 hours in dry air. The resultant catalysts were analyzed for wt. % Pt, wt. % F, and wt. % Cl by x-ray florescence (XRF) and porosity was determined by nitrogen adsorption and calculated by the Brunauer-Emmett-Teller (BET) method. Analysis of these catalysts is summarized in Table 3.

TABLE 3

Analysis of Catalysts

| | | | Pt/KL Catalyst | | | | | |
|---|---|---|---|---|---|---|---|---|
| Support Example | Support Description | Treatment Temp (° C.) | Catalyst Example | F (wt. %) | Cl (wt. %) | Pt (wt. %) | Surface Area (m²/g) | Pore Volume (cc/g) | Micropore volume (cc/g) |
| C | WCEB | untreated | control | 0.92 | 0.91 | 0.98 | 201.6 | 0.212 | 0.074 |
| A | EB | 500 | A | 0.37 | 0.52 | 0.94 | 55.1 | 0.149 | 0.015 |
| B | CEB | 500 | B | 0.35 | 0.53 | 0.97 | 48.6 | 0.155 | 0.012 |
| C | WCEB | 350 | G | 0.55 | 0.46 | 0.99 | 82.0 | 0.142 | 0.029 |
| C | WCEB | 350 | F | 0.57 | 0.48 | 0.99 | 77.6 | 0.125 | 0.027 |
| C | WCEB | 400 | E | 0.43 | 0.40 | 0.98 | 94.7 | 0.178 | 0.028 |
| C | WCEB | 450 | D | 0.44 | 0.42 | 0.96 | 66.4 | 0.130 | 0.020 |
| C | WCEB | 500 | C | 0.27 | 0.42 | 0.99 | 53.8 | 0.112 | 0.017 |

Aromatization Performance Examples

In the following examples, the catalysts prepared above were aromatization catalysts of the type described previously herein. Each of the catalysts was evaluated for performance as an aromatization catalyst. In each of the following examples the following standard test conditions were utilized, the catalysts were ground, sieved to about 20 to 40 mesh, and 1 gram was placed in a reactor comprising a ¼ inch OD stainless steel reactor vessel in a temperature controlled furnace. After reducing the catalyst under flowing hydrogen, a feed stream of aliphatic hydrocarbon and hydrogen was introduced to the reactor vessel at a feed rate of 22 mL/min; a pressure of 50 psig (345 kPa); a $H_2$:Hydrocarbon mole ratio of 3:1, a liquid hourly space velocity of 9 $hr^{-1}$, to obtain performance data. The aliphatic hydrocarbon contained the following weight percentages of normal paraffins and isoparaffins; about 8 wt. % $C_8$ paraffins, about 28 wt. % $C_7$ paraffins, and about 62 wt. % $C_6$ paraffins. The reactor effluent composition was analyzed by gas chromatography to indicate the amount of benzene and toluene present in the product as well as the amount of light hydrocarbons with four or fewer carbons ($C_4^-$ wt %). Low severity conditions were adjusted to give a total of 60 wt. % for the sum of the benzene wt. % and toluene wt. % in the reactor effluent while high severity conditions were adjusted to give a total of 75 wt. % for the sum of the benzene wt. % and toluene wt. % in the reactor effluent. The catalyst performance was determined by plotting the temperature required to maintain a total yield of benzene plus toluene at 60 wt. % for low severity conditions (75 wt. % for high severity conditions) over time at standard test conditions. In each of the following examples the catalyst preparation procedure, preparation parameters, and/or the process condition variations are evaluated by the effects observed in $T_{60}$ or $T_{75}$, as well as the $C_4^-$ wt. %. Other parameters tabulated include time on-stream (hr) (also denoted TOS); and benzene toluene mole ratio in the product as presented in Table 4.

TABLE 4

Evaluation of Catalysts

| | | | Pt/KL Aromatization Catalyst Performance | | | | | | | |
|---|---|---|---|---|---|---|---|---|---|---|
| | | | Low Severity (B + T = 60%) | | | | High Severity (B + T = 75%) | | | |
| Support Description | Treatment Temp (° C.) | Catalyst Example | TOS hr | $C_4^-$ wt. % | $T_{60}$ ° F. (° C.) | B/T mole ratio | TOS hr | $C_4^-$ wt. % | $T_{75}$ ° F. (° C.) | B/T mole ratio |
| WCEB | untreated | control | 47.9 | 2.3 | 906 (486) | 2.0 | 78.1 | 3.75 | 959 (515) | 2.6 |
| EB | 500 | A | 48.1 | 2.2 | 904 (484) | 2.0 | 78.6 | 3.52 | 957 (514) | 2.6 |
| CEB | 500 | B | 48.2 | 2.1 | 902 (483) | 1.9 | 78.9 | 3.33 | 959 (515) | 2.4 |
| WCEB | 350 | G | 45.1 | 2.7 | 915 (491) | 2.1 | 75.9 | 5.48 | 994 (534) | 2.8 |
| WCEB | 350 | F | 51.0 | 3.2 | 913 (489) | 2.0 | 73.9 | 4.54 | 965 (518) | 2.5 |
| WCEB | 400 | E | — | — | — | — | — | — | — | — |
| WCEB | 450 | D | — | — | — | — | — | — | — | — |
| WCEB | 500 | C | 48.0 | 2.5 | 903 (484) | 1.9 | 78.6 | 4.05 | 955 (513) | 2.7 |

The results demonstrate that treatment of the extruded base, the calcined extruded base or washed calcined extruded base with fluoride decreases the micro porosity of the support and the resultant aromatization catalyst, and that treatment of the extruded base (Catalyst A) and calcined extruded base (Catalyst B) gives greater aromatization catalyst selectivity as judged by the lower wt. % $C_4^-$ in the product.

The following enumerated aspects are provided as non-limiting examples of the subject matter of the present disclosure.

Crush Strength Examples

In the following examples, twice fluorided catalysts were tested for crush strength, and compared with the crush strength of catalysts that are only once fluorided.

The Pt—Cl—F on F-CEB catalyst was prepared by blending a K-L zeolite powder, a silica binder, and water to form a paste and shaping the paste into a wet extruded base (WEB). The WEB was dried to form a dried extruded base (EB). The EB was then calcined to form a calcined extruded base (CEB). The CEB was then be contacted with $NH_4F$ to form a fluorinated calcined extruded base (F-CEB). The F-CEB was then calcined, washed, dried, and again calcined to form a bound zeolite support. The bound zeolite support was then contacted with Pt, $NH_4Cl$, and $NH_4F$, then dried, and then again calcined to form the Pt—Cl—F on F-CEB catalyst. Thus, "Pt—Cl—F on F-CEB" indicates that the support was contacted with a fluorine-containing compound at two points during catalyst preparation: 1) a fluorine-containing compound was added to the calcined extruded base and 2) a fluorine-containing compound was added with Pt and a chlorine-containing compound during metal addition to the bound zeolite support. The "Pt—Cl—F on F-CEB catalyst" may also be referred to as a twice fluorided Pt—Cl—F catalyst or a pre-fluorided Pt—Cl—F catalyst.

The Pt—Cl—F on CEB catalyst was prepared by blending a K-L zeolite powder, a silica binder, and water to form a paste and shaping the paste into a wet extruded base (WEB). The WEB was dried to form a dried extruded base (EB). The EB was then calcined to form a calcined extruded base (CEB). The CEB was then washed, dried, and again calcined to form a bound zeolite support. The bound zeolite support was then contacted with Pt, $NH_4Cl$, and $NH_4F$, then dried, and then again calcined to form the Pt—Cl—F on CEB catalyst. Thus, "Pt—Cl—F on CEB" indicates that a fluorine-containing compound was added with Pt and a chlorine-containing compound during metal addition to the bound zeolite support, but was not added to the WEB, EB, or CEB before metal addition. The "Pt—Cl—F on CEB catalyst" may also be referred to as a once fluorided Pt—Cl—F catalyst, which has not been pre-fluorided.

The Pt—Cl on F-CEB catalyst was prepared by blending a K-L zeolite powder, a silica binder, and water to form a paste and shaping the paste into a wet extruded base (WEB). The WEB was dried to form a dried extruded base (EB). The EB was then calcined to form a calcined extruded base (CEB). The CEB was then be contacted with $NH_4F$ to form a fluorinated calcined extruded base (F-CEB). The F-CEB was then calcined, washed, dried, and again calcined to form a bound zeolite support. The bound zeolite support was then contacted with Pt and $NH_4Cl$, then dried, and then again calcined to form the Pt—Cl on F-CEB catalyst. Thus, "Pt—Cl on F-CEB" indicates that a fluorine-containing compound was added to the calcined extruded base, but was not added with Pt and a chlorine-containing compound during metal addition to the bound zeolite support. The "Pt—Cl on F-CEB catalyst" may also be referred to as a once fluorided Pt—Cl—F catalyst or a pre-fluorided Pt—Cl catalyst.

Table 5 below reports data related to crush strength for each of the Pt—Cl—F on F-CEB catalyst, Pt—Cl—F on CEB catalyst, and Pt—Cl on F-CEB catalyst.

The average crush strength for each catalyst was obtained by i) obtaining two samples of each catalyst, where each sample contained 50 catalyst pellets, ii) measuring the individual crush strength of each catalyst pellet in accordance with ASTM D4179, except the dry out step required by ASTM D4179 was performed at 538° C. instead of 400° C., iii) calculating a sample crush strength as the average of the individual pellet crush strengths for each sample, and iii) calculating the average crush strength for each catalyst as the average of the sample crush strengths from the two samples. In Table 5, the crush strength value reported for each of "Sample A", "Sample B", "Sample C", "Sample D", "Sample E", and "Sample F" is the sample crush strength, or average of the individual pellet crush strengths, for each Sample A to F. The crush strength values reported as "Avg AB", Avg CD", and "Avg EF" are the average crush strength, or average of the sample crush strengths of the two respective samples (i.e., AB, CD, or EF), for each catalyst.

The "crush strength per length" was determined by i) measuring the length of each pellet before measuring its individual crush strength as described above, ii) dividing the individual crush strength that is measured for each pellet in accordance with ASTM D4179 by the measured length to obtain an individual pellet crush strength per length for each pellet, iii) calculating a sample crush strength per length as the average of the individual pellet crush strengths per length for each sample, and iv) calculating the average crush strength per length for each catalyst as the average of the sample crush strengths per length for the two samples of each catalyst. In Table 5, the crush strength per length value reported for each of "Sample A", "Sample B", "Sample C", "Sample D", "Sample E", and "Sample F" is the sample crush strength per length, or average of the individual pellet crush strength per length, for each Sample A to F. The crush strength per length values reported as "Avg AB", Avg CD", and "Avg EF" are the average crush strength per length, or average of the sample crush strengths per length of the two respective samples (i.e., AB, CD, or EF), for each catalyst.

Table 5 also shows the "Crush Strength <10 lb" for "Sample A", "Sample B", "Sample C", "Sample D", "Sample E", and "Sample F", which is the number % of the 50 pellets in each sample of each catalyst that had a crush strength of less than 10 lb. The "Crush Strength <10 lb" values reported as "Avg AB", Avg CD", and "Avg EF" are the average "Crush Strength <10 lb" of the two respective samples for each catalyst.

Also in Table 5, "Crush <9 lb" for "Sample A", "Sample B", "Sample C", "Sample D", "Sample E", and "Sample F" is the number % of the 50 pellets in each sample of each catalyst that had a crush strength of less than 9 lb. The "Crush Strength <9 lb" values reported as "Avg AB", Avg CD", and "Avg EF" are the average "Crush Strength <9 lb" of the two respective samples for each catalyst.

TABLE 5

Catalyst Crush Strength

| Catalyst | | Crush Strength (lb) | Crush Strength per Length (lb/mm) | Crush Strength <10 lb (%) | Crush Strength <9 lb (%) |
|---|---|---|---|---|---|
| Pt—Cl—F on F-CEB | Sample A | 13.67 | 2.74 | 14 | 10 |
| | Sample B | 13.14 | 3.27 | 20 | 14 |
| | Avg AB | 13.41 | 3.01 | 17 | 12 |
| Pt—Cl—F on CEB | Sample C | 10.59 | 2.08 | 46 | 30 |
| | Sample D | 11.91 | 2.41 | 26 | 22 |
| | Avg CD | 11.25 | 2.25 | 36 | 26 |
| Pt—Cl on F-CEB | Sample E | 11.87 | 2.31 | 24 | 14 |
| | Sample F | 11.71 | 2.65 | 22 | 16 |
| | Avg EF | 11.79 | 2.47 | 23 | 15 |

As can be seen, the average crush strength and each sample crush strength for the Pt—C—F on F-CEB catalyst are higher than corresponding crush strengths of the Pt—Cl—F on CEB catalyst and the Pt—Cl on F-CEB catalyst. The average crush strength per length and the sample crush strength per length for the Pt—Cl—F on F-CEB catalyst are also higher than the corresponding crush strengths per length of the Pt—Cl—F on CEB catalyst and the Pt—Cl on F-CEB catalyst. The Pt—Cl—F on F-CEB catalyst had a smaller amount of pellets with crush strength <10 lb and <9 lb compared to the Pt—Cl—F on CEB catalyst and the Pt—Cl on F-CEB catalyst.

It is believed that the higher crush strength, as well as the lower number % of pellets having a crush strength less than 10 lb and 9 lb, are indicative that the Pt—Cl—F on F-CEB catalyst will produce fewer catalyst fines when catalyst particles are moved (e.g., catalyst loading and unloading), and thus, the severity of problems associated with fines will be reduced, compared to the amount of fines that would be produced when using the Pt—Cl—F on CEB catalyst and the Pt—Cl on F-CEB catalyst.

Additional Description

The following is provided as additional disclosure for combinations of features and aspects of the present invention.

A first aspect which is a method of preparing a bound zeolite support comprising contacting a zeolite powder with a binder and water to form a paste; shaping the paste to form an wet extruded base; removing excess water from the wet extruded base to form an extruded base; contacting the extruded base with a fluorine-containing compound to form a fluorinated extruded base; calcining the extruded base to form a calcined fluorinated extruded base; washing the calcined fluorinated extruded base to form a washed calcined fluorinated extruded base; drying the washed calcined fluorinated extruded base to form a dried washed calcined fluorinated extruded base; and calcining the dried washed calcined fluorinated extruded base to form a bound zeolite support.

A second aspect which is a method of preparing a bound zeolite support comprising contacting a zeolite powder with a binder and water to form a paste; shaping the paste to form an wet extruded base; removing excess water from the wet extruded base to form a extruded base; calcining the extruded base to form a calcined extruded base; contacting the calcined extruded base with a fluorine-containing compound to form a fluorinated calcined extruded base; washing the fluorinated calcined extruded base to form a washed fluorinated calcined extruded base; drying the washed fluorinated calcined extruded base to form a dried washed fluorinated calcined extruded base; and calcining the dried washed fluorinated calcined extruded base to form a bound zeolite support.

A third aspect which is a method of preparing a bound zeolite support comprising contacting a zeolite powder with a binder and water to form a paste; shaping the paste to form an extruded base; calcining the extruded base to form a calcined extruded base; contacting the calcined extruded base with a fluorine-containing compound to form a fluorinated calcined extruded base; washing the fluorinated calcined extruded base to form a washed fluorinated calcined extruded base; drying the washed fluorinated calcined extruded base to form a dried washed fluorinated calcined extruded base; and calcining the dried washed fluorinated calcined extruded base to form a bound zeolite support.

A fourth aspect which is the method of any preceding aspect wherein the fluorine-containing compound is in the gas phase.

A fifth aspect which is the method of any preceding aspect wherein the binder comprises synthetic or naturally-occurring zeolites, alumina, silica, clays, refractory oxides of metals of Groups IVA and IVB of the Periodic Table of the Elements; oxides of silicon, titanium, zirconium; or combinations thereof.

A sixth aspect which is the method of any preceding aspect wherein the bound zeolite support has a weight ratio of the zeolite to the binder in a range of from about 90:10 to about 70:30.

A seventh aspect which is the method of any preceding aspect wherein the zeolite comprises a large pore zeolite.

An eighth aspect which is the method of any preceding aspect wherein the zeolite comprises a KL-zeolite.

A ninth aspect which is the method of any preceding aspect wherein the fluorine-containing compound is an organic ammonium halide compound represented by the general formula $N(R)_4F$, where R represents a hydrogen or a substituted or unsubstituted carbon chain molecule having from 1 to 20 carbon atoms and wherein each R may be the same or different.

A tenth aspect which is the method of any preceding aspect wherein R is methyl, ethyl, propyl, butyl, or combinations thereof.

An eleventh aspect which is the method of any preceding aspect wherein the fluorine-containing compound comprises ammonium fluoride, tetramethylammonium fluoride, tetraethylammonium fluoride, tetrapropylammonium fluoride, tetrabutylammonium fluoride, methyltriethylammonium fluoride, or combinations thereof.

A twelfth aspect which is the method of any preceding aspect wherein the bound zeolite support comprises fluoride present in an amount of from about 0.1 wt. % to about 5 wt. % based on x-ray florescence.

A thirteenth aspect comprising contacting the bound zeolite support of any preceding aspect with a Group VIII metal and at least one chlorine-containing compound to form an aromatization catalyst.

A fourteenth aspect which is the method of the thirteenth aspect wherein the Group VIII metal comprises platinum.

A fifteenth aspect which is the method of any of the fourteenth through fifteenth aspects wherein the chlorine-containing compound is an organic ammonium halide compound represented by the general formula $N(R)_4Cl$, where R represents a hydrogen or a substituted or unsubstituted carbon chain molecule having from 1 to 20 carbon atoms and wherein each R may be the same or different.

A sixteenth aspect which is a catalytic reforming process for converting hydrocarbons to aromatics comprising: contacting the aromatization catalyst of any preceding aspect with a hydrocarbon feed in a reaction zone under reforming conditions and recovering aromatics from the reaction zone.

A seventeenth aspect which is the catalytic reforming process of the sixteenth aspect wherein the hydrocarbon feed contains less than 100 ppb of sulfur.

An eighteenth aspect which is the catalytic reforming process of any of the sixteenth through seventeenth aspects wherein the aromatization catalyst has a selectivity of from about 20% to 100% as determined by weight percent yield of $C_5^+$.

A nineteenth aspect which is a catalyst comprising: a zeolite support; a Group VIII metal on the zeolite support; and at least two halides bound to the zeolite support, to the Group VIII metal, or to both, wherein an average crush strength of the catalyst is greater than 11.25 lb based on at least two samples of pellets of the catalyst measured in accordance with ASTM D4179.

A twentieth aspect which is the catalyst of the nineteenth aspect, wherein each of the at least two samples of pellets has 50 pellets.

A twenty-first aspect which is the catalyst of any of the nineteenth and the twentieth aspects, wherein the average crush strength is greater than 12 lb based on at least two samples of pellets of the catalyst measured in accordance with ASTM D4179.

A twenty-second aspect which is the catalyst of any of the nineteenth through the twenty-first aspects, wherein an average crush strength per length of the catalyst is greater than about 2.48 lb/mm.

A twenty-third aspect which is the catalyst of any of the nineteenth through the twenty-second aspects, wherein the average crush strength per length of the catalyst is in a range of from about 3.00 lb/mm to about 3.10 lb/mm.

A twenty-fourth aspect which is the catalyst of any of the nineteenth through the twenty-third aspects, wherein less than 22% of the pellets that are measured in accordance with ASTM D4179 have an individual pellet crush strength of less than 10 lb/pellet.

A twenty-fifth aspect which is the catalyst of any of the nineteenth through the twenty-fourth aspects, wherein less than 21% of the pellets that are measured in accordance with ASTM D4179 have an individual pellet crush strength of less than 10 lb/pellet.

A twenty-sixth aspect which is the catalyst of any of the nineteenth through the twenty-fifth aspects, wherein less than 14% of the pellets that are measured in accordance with ASTM D4179 have an individual pellet crush strength of less than 9 lb/pellet.

A twenty-seventh aspect which is the catalyst of any of the nineteenth through the twenty-sixth aspects, wherein less than 13% of the pellets that are measured in accordance with ASTM D4179 have an individual pellet crush strength of less than 9 lb/pellet.

A twenty-eighth aspect which is the catalyst of any of the nineteenth through the twenty-seventh aspects, wherein the zeolite support comprises a KL-zeolite.

A twenty-ninth aspect which is the catalyst of any of the nineteenth through the twenty-eighth aspects, wherein the zeolite support further comprises a binder, wherein the binder comprises synthetic or naturally-occurring zeolites, alumina, silica, clays, refractory oxides of metals of Groups IVA and IVB of the Periodic Table of the Elements; oxides of silicon, titanium, zirconium; or combinations thereof.

A thirtieth aspect which is the catalyst of any of the nineteenth through the twenty-ninth aspects, wherein the Group VIII metal is Pt.

A thirty-first aspect which is the catalyst of any of nineteenth through the thirtieth aspects, wherein the at least two halides comprise fluoride and chloride.

A thirty-second aspect which is a method of preparing a catalyst comprising calcining an extruded base to form a calcined extruded base, wherein the extruded base comprises a KL-zeolite, contacting the calcined extruded base with a first fluorine-containing compound to form a fluorinated calcined extruded base, washing the fluorinated calcined extruded base to form a washed fluorinated calcined extruded base, drying the washed fluorinated calcined extruded base to form a dried washed fluorinated calcined extruded base, calcining the dried washed fluorinated calcined extruded base to form a bound zeolite support, and contacting the bound zeolite support with a Group VIII metal and a second fluorine-containing compound, wherein the first fluorine-containing compound and the second fluorine-containing compound may be the same or different.

A thirty-third aspect which is the method of the thirty-second aspect, further comprising contacting the bound zeolite support with a chlorine-containing compound.

A thirty-fourth aspect which is the method of the thirty-third aspect, wherein the bound zeolite support is contacted with the chlorine-containing compound while the bound zeolite support is contacted with the Group VIII metal and with the second fluorine-containing compound.

A thirty-fifth aspect which is the method of the thirty-third or thirty-fourth aspects, wherein the chlorine-containing compound is an organic ammonium halide compound represented by the general formula $N(R)_4Cl$, where R represents a hydrogen or a substituted or unsubstituted carbon chain molecule having from 1 to 20 carbon atoms and wherein each R may be the same or different.

A thirty-sixth aspect which is the method of any of the thirty-second through the thirty-fifth aspects, wherein the first fluorine-containing compound and the second fluorine-containing compound are independently selected from tetramethylammonium fluoride (TMAF) and ammonium fluoride ($NH_4F$).

A thirty-seventh aspect which is the method of any of the thirty-second through the thirty-sixth aspects, wherein the Group VIII metal is Pt.

A thirty-eighth aspect which is the method of any of the thirty-second through the thirty-seventh aspects, further comprising after contacting the bound zeolite support with the Group VIII metal and the second fluorine-containing compound, drying and then calcining the bound zeolite support to form the catalyst.

While aspects of the present disclosure have been shown and described, modifications thereof may be made by one skilled in the art without departing from the spirit and teachings of the disclosure. The aspects described herein are exemplary only, and are not intended to be limiting. Many variations and modifications of the disclosure are possible and are within the scope of the invention. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the preferred aspects of the present invention. The discussion of a reference in the Background is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed it is intended to disclose or claim individually each possible number that such a range could reasonably encompass, including any subranges encompassed therein. When describing a range of measurements every possible number that such a range could reasonably encompass may, for example, refer to values within the range with one significant digit more than is present in the end points of a range. Moreover, when a range of values is disclosed or claimed, which Applicants intent to reflect individually each possible number that such a range could reasonably encompass, Applicants also intend for the disclosure of a range to reflect, and be interchangeable with, disclosing any and all subranges and combinations of subranges encompassed therein. Accordingly, Applicants reserve the right to proviso out or exclude any individual members of any such group, including any subranges or combinations of subranges within the group, if for any reason Applicants choose to claim less than the full measure of the disclosure.

What is claimed is:

1. A method of preparing a catalyst comprising:
   calcining an extruded base to form a calcined extruded base, wherein the extruded base comprises a KL-zeolite and a binder;
   contacting the calcined extruded base with a first fluorine-containing compound to form a fluorinated calcined extruded base;
   washing the fluorinated calcined extruded base to form a washed fluorinated calcined extruded base;
   drying the washed fluorinated calcined extruded base to form a dried washed fluorinated calcined extruded base;
   calcining the dried washed fluorinated calcined extruded base to form a bound zeolite support; and
   contacting the bound zeolite support with a Group VIII metal and a second fluorine-containing compound and after contacting the bound zeolite support with the Group VIII metal and the second fluorine-containing compound, drying and then calcining the bound zeolite support to form the catalyst,
   wherein the average crush strength of the catalyst is greater than 12 lb based on at least two samples of pellets of the catalyst measured in accordance with ASTM D4179, and
   wherein the first fluorine-containing compound and the second fluorine-containing compound may be the same or different.

2. The method of claim 1, further comprising contacting the bound zeolite support with a chlorine-containing compound.

3. The method of claim 2, wherein the bound zeolite support is contacted with the chlorine-containing compound while the bound zeolite support is contacted with the Group VIII metal and with the second fluorine-containing compound.

4. The method of claim 2, wherein the chlorine-containing compound is an organic ammonium halide compound represented by the general formula $N(R)_4Cl$, where R represents a hydrogen or a substituted or unsubstituted carbon chain molecule having from 1 to 20 carbon atoms and wherein each R may be the same or different.

5. The method of claim 2, wherein the chlorine-containing compound is ammonium chloride, tetramethylammonium chloride, tetraethylammonium chloride, tetrapropylammonium chloride, tetrabutylammonium chloride, methyltriethylammonium chloride, or combinations thereof.

6. The method of claim 2, wherein the chlorine-containing compound is ammonium chloride.

7. The method of claim 1, wherein the first fluorine-containing compound and the second fluorine-containing compound are independently selected from tetramethylammonium fluoride (TMAF) and ammonium fluoride ($NH_4F$).

8. The method of claim 1, wherein the fluorine-containing compound is in the gas phase.

9. The method of claim 1, wherein the bound zeolite support has a weight ratio of the KL-zeolite to the binder in a range of from about 90:10 to about 70:30.

10. The method of claim 1, wherein the KL-zeolite comprises pores having an effective pore diameter ranging from about 6 Angstroms (Å) (0.6 nm) to about 15 Å (1.5 nm).

11. The method of claim 1, wherein the bound zeolite support comprises fluoride present in an amount of from about 0.1 wt. % to about 5 wt. % based on x-ray florescence.

12. The method of claim 1, wherein the Group VIII metal is Pt.

13. The method of claim 1, wherein an average crush strength per length of the catalyst is greater than about 2.48 lb/mm.

14. The method of claim 1, wherein the average crush strength per length of the catalyst is in a range of from about 3.00 lb/mm to about 3.10 lb/mm.

15. The method of claim 1, wherein less than 22% of the pellets that are measured in accordance with ASTM D4179 have an individual pellet crush strength of less than 10 lb/pellet.

16. The method of claim 1, wherein less than 21% of the pellets that are measured in accordance with ASTM D4179 have an individual pellet crush strength of less than 10 lb/pellet.

* * * * *